United States Patent [19]

Narayan

[11] Patent Number: 5,637,475
[45] Date of Patent: Jun. 10, 1997

[54] TIME-TEMPERATURE METHOD FOR ESTABLISHING LETHALITY OF HIGH TEMPERATURE FOOD PROCESSING

[75] Inventor: K. Ananth Narayan, Framingham, Mass.

[73] Assignee: The United States of America as represented by the Secretary of the Army, Washington, D.C.

[21] Appl. No.: 262,290

[22] Filed: Jun. 20, 1994

Related U.S. Application Data

[62] Division of Ser. No. 215,797, Mar. 16, 1994.

[51] Int. Cl.[6] ............................ C12Q 1/04; C12Q 1/02; G01N 7/00
[52] U.S. Cl. ........................... 435/31; 435/4; 435/34; 435/808; 435/810; 422/83; 422/86; 422/101
[58] Field of Search .................. 435/4, 29, 31, 435/296, 832, 34, 288, 808, 810; 422/83, 86, 101

[56] References Cited

U.S. PATENT DOCUMENTS

| | | | |
|---|---|---|---|
| 2,950,202 | 8/1960 | Brockmann | 435/31 |
| 3,260,112 | 7/1966 | Godbey et al. | 73/356 |
| 3,960,670 | 6/1976 | Pflug | 195/103.5 R |
| 3,993,795 | 11/1976 | Mauron | 426/618 |
| 4,533,640 | 8/1985 | Shafer | 436/2 |
| 4,732,850 | 3/1988 | Brown et al. | 435/31 |
| 4,743,557 | 5/1988 | Tiru et al. | 436/2 |
| 4,834,017 | 5/1989 | Favetto et al. | 116/207 |
| 4,839,291 | 6/1989 | Welsh et al. | 435/296 |
| 5,182,212 | 1/1993 | Jalinski | 436/2 |
| 5,223,401 | 6/1993 | Foltz | 435/18 |

*Primary Examiner*—Donald E. Czaja
*Assistant Examiner*—Jane Williams
*Attorney, Agent, or Firm*—John H. Lamming; Vincent J. Ranucci

[57] ABSTRACT

There is presented a time-temperature indicator method for determining lethality of high-temperature food processing using a capsule comprising a cylindrical tube having a closed end and an open end, a cap for connection to and removal from the open end to close and open the tube, and a solution in the tube which is reactive to accumulated temperature and time exposure to fluoresce proportionally to the accumulated temperature and time exposure. There is further presented a time-temperature indicator system including the above capsule, a pipetting device for removing the solution from the capsule, and a spectrofluorometer for indicating the fluorescence of the solution, said fluorescence being directly correlatable to the time-temperature integral $F_0$ by linear regression. There is still further presented methods for determining when food processed under high temperature conditions attains a selected low level of microbial population, the methods utilizing, respectively, the above systems.

15 Claims, 6 Drawing Sheets

TIME-TEMPERATURE METHOD FOR ESTABLISHING LETHALITY OF HIGH TEMPERATURE FOOD PROCESSING

This application is a division of copending application Ser. No. 08/215,797, filed Mar. 16, 1994.

STATEMENT OF GOVERNMENT INTEREST

The invention described herein may be manufactured, used and licensed by or for the U.S. Government for U.S. Governmental purposes without the payment to us of any royalty thereon.

BACKGROUND OF THE INVENTION

(1) Field of the Invention

The invention relates to a device, systems, and methods for determining the cumulative effects of time and temperature upon matter subjected to heat over a period of time and is directed more particularly to a reusable capsule adapted for use in high-temperature food processing and to systems and methods for establishing the lethality of time and temperature during food processing.

(2) Description of the Prior Art

Thermal processing of foods is directed towards reaching sterility to a selected low level of microbial population, which usually is expressed as "12 log" reductions of the initial microbial population. In most food processing, the pathogenic organism targeted is *Clostridium botulinum*. It has been established that a 12 log reduction in its population is achieved by heating low-acid foods at 250° F. (121.1° C.) for six minutes, usually stated as a time-temperature integral, or "Fo" of six minutes, or by heating at equivalent time-temperature combinations.

The time-temperature integral, Fo, is computed by integration of the time and temperature of the food product, taking into consideration a temperature sensitivity, or Z "value" of the target organism. Fo is computed from the equation:

$$F_0 = \int_0^t 10^{(T-T_{ref})/z} dt$$

wherein

T equals the running temperature of the processing operation,

T ref. equals 250° F. (121.1° C.) and

Z=18° F. (10° C.) for *C. botulinum* spores.

In an everchanging temperature environment during food processing, as in a retort, wherein the temperature of the food particles in a cylindrical can or rectangular tray pack continuously increases to the usually selected value of 250° F. (121.1° C.), the time-temperature integral, Fo, provides an accumulation of lethality units until the heating and cooling of the food is terminated.

In a substantially static situation, as in beef cubes heated in a tray pack, thermocouples are inserted into the center of the cubes to provide an indication of the temperature to which the food particles are heated. The integration of time and temperature with necessary modulation based upon the temperature sensitivity factor Z of the target food microorganism, in accordance with the above equation, provides an indication as to when the target Fo has been reached and therefore when to terminate the processing.

Unfortunately, even under substantially ideal conditions, there are some difficulties, such as site-specific temperature differences, pressure fluctuations during sterilization, and viscosity/thermal conductivity changes of the food particulates. In the case of continuous food processing devices, such as aseptic processing devices, wherein food particles are heated as they are pumped through a heat exchanger, it is not possible to insert thermocouples in the moving food particles to record the time-temperature history of the food particles.

Accordingly, there exists a need during food processing for a time-temperature indicator which can be utilized with continuously flowing foods, as well as relatively static foods and which may be used in high temperature (110°–138° C.) situations.

SUMMARY OF THE INVENTION

An object of the invention is, therefore, to provide a time-temperature indicator for use in monitoring and predicting lethality of high temperature food processing operations.

Another object of the invention is to provide such an indicator in reusable capsule form, such that the indicator may be used time and again in flowing foods and/or static foods and in solids and liquids.

A still further object of the invention is to provide such a capsule having means for highly sensitive detection, correlating accurately and reliably with Fo values.

With the above and other objects in view, as will hereinafter appear, a feature of the present invention is the provision of a time-temperature indicator capsule (TTIC) comprising a substantially cylindrical tube having a closed-end and an open end, a cap for connection to and removal from the open end of the tube to close and open the tube at the open end, and a solution in the tube which is reactive to accumulated temperature and time exposure to fluoresce proportionally to the accumulated temperature and time exposure.

In accordance with a further feature of the invention, there is provided a time-temperature indicator system comprising a capsule having a chamber therein, a solution in the capsule chamber reactive to accumulated temperature and time exposure to fluoresce proportionally to the accumulated temperature and time exposure, a pipetting device for removing the solution from the capsule chamber, and a spectrofluorometer for receiving the solution from the pipetting device and for providing a fluorescence reading indicative of the aggregate thermal effect on the solution.

In accordance with a still further feature of the invention, there is provided a method for determining when food processed under high temperature conditions attains a selected low level of microbial population, the method comprising the steps of providing a stainless steel capsule having a chamber therein, providing in said chamber a solution reactive to accumulated temperature and time exposure to fluoresce proportionally to the accumulated temperature and time exposure, placing the capsule inside particulates of food, or proximate the food, processing the food by subjecting the food to temperatures in the range of 110° C. to 138° C. for a selected time period, removing the capsule from the processing after a selected time, pipetting a sample of the solution from the capsule, diluting the pipetted solution with deionized water, and placing the diluted solution in a spectrofluorometer to obtain, by reading the fluorescence of the pipetted and diluted solution, the accumulative effects of the time and temperature to which the food was exposed.

In accordance with a still further feature of the invention, there is provided an alternative method for determining when food processed under high temperature conditions attains a selected low level of microbial population, the method comprising the steps of providing a capsule having a chamber therein, providing in the chamber a solution of bacterial spores reactive to accumulated temperature and time exposure to degrade proportionally to the accumulated temperature and time exposure, placing the capsule inside particulates of food or proximate to the food, processing the food by subjecting the food to temperatures in the range of 110° C. to 138° C. for a selected time period, removing the capsule from the processing after a selected time, pipetting a sample of the solution from the capsule, and placing at least a portion of the sample on an agar plate having required nutrients and other additives thereon, for providing a count of the surviving spores, which count is indicative of the aggregate thermal effects on the solution.

The above and other features of the invention, including various novel details of construction and combination of parts, will now be more particularly described with reference to the accompanying drawings and pointed out in the claims. It will be understood that the particular devices and methods embodying the invention are shown by way of illustration only and not as limitations of the invention. The principles and features of the invention may be employed in various and numerous embodiments without departing from the scope of the invention.

BRIEF DESCRIPTION OF THE DRAWINGS

Reference is made to the accompanying drawings in which are shown illustrative embodiments of the invention, from which its' novel features and advantages will be apparent.

In the drawings.

DESCRIPTION OF THE PREFERRED EMBODIMENTS

Figure 1:
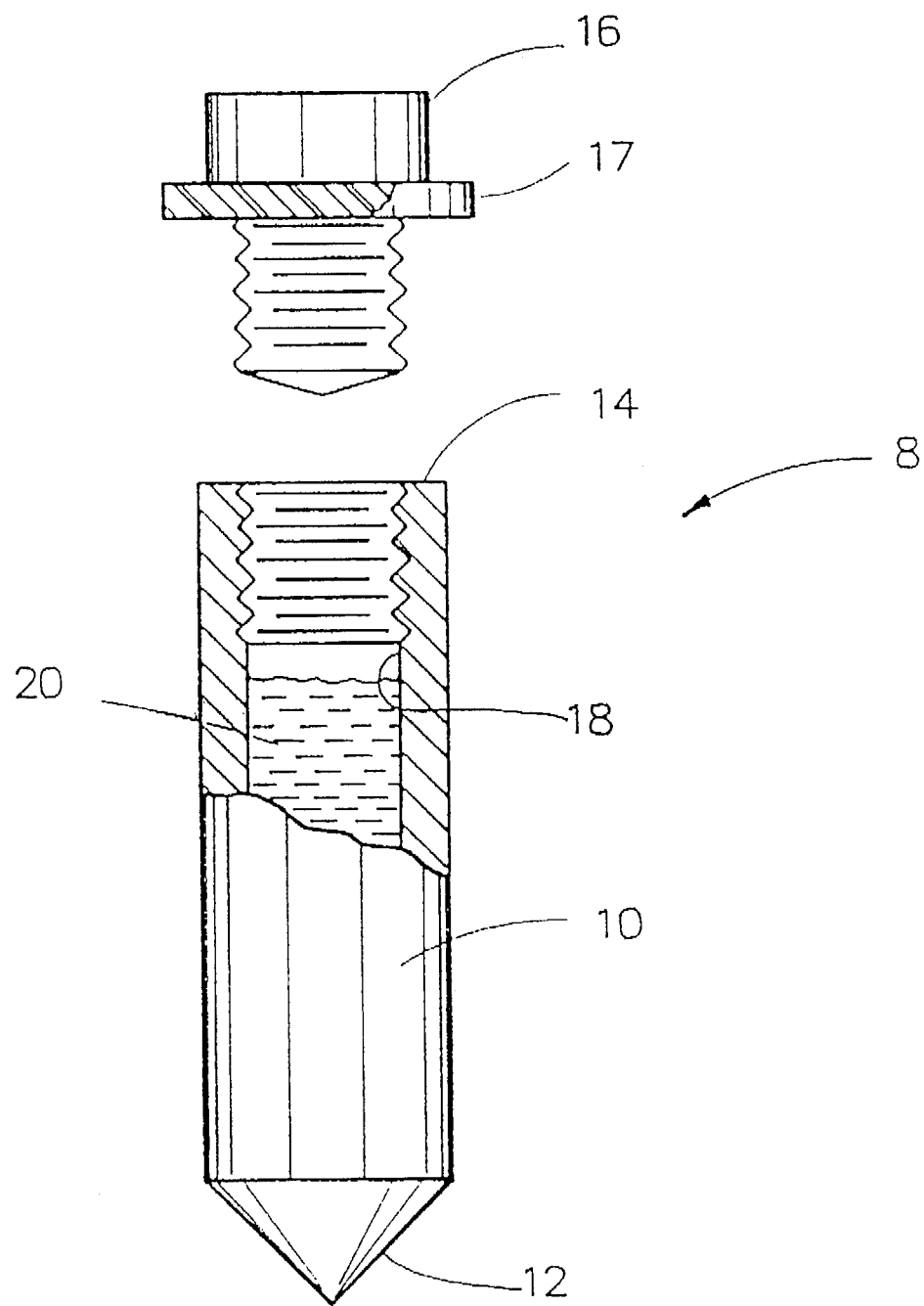
FIG. 1 is an exploded view, partly in section, of one form of a capsule, illustrative of an embodiment of the invention.

Referring to FIG. 1, it will be seen that an illustrative capsule 8 includes a cylindrical tube 10, preferably of stainless steel, having a closed end 12 and an open end 14. Threadedly engageable with the open end 14 of the tube 10 is a cap 16, also preferably of stainless steel, for closing the open end 14 of the tube 10 and sealing closed a chamber 18. The cap 16 is provided with a nylon washer 17. Disposed in the chamber 18 is a solution 20 which is reactive to accumulated temperature and time exposure to fluoresce proportionally to the accumulated temperature and time exposure experienced by the solution.

The tube 10 and the cap 16 connected together, provide the capsule 8 with a length of about three quarters of an inch and a radius of about 1/16 inch. A wall thickness of about 1/64 inch has been found appropriate for the stainless steel capsule, providing the capsule with facility for holding steam pressure of up to 50 p.s.i. The chamber 18 is provided with a capacity of about 25 microliters.

The solution 20 comprises lysine and glucose, preferably about 0.05 molar lysine and about 0.15 molar glucose in a phosphate buffer having a pH of about 8.0. The chamber 18 of the capsule 8 is sized to retain about 15–25 microliters of the solution 20.

The capsule 8 is reusable and is not deleteriously affected structurally by exposure to temperature in the range of 110°–138° C.

The solution 20 fluoresces in a manner correlating well with Fo values, is extremely sensitive to time-temperature conditions, and is well adapted to operations in the above-mentioned high temperature range.

Any number of the capsules 8 may be inserted anywhere along a food processing line, in either liquids or solids, or may be anchored on a tray, heating tube, or the like.

The capsule, with the solution 20 therein, provides a proportional chemical time-temperature indicator, based upon the degradation kinetics, at the afore-mentioned high temperature, of the solution of 0.05 molar lysine, 0.15 molar glucose and phosphate buffer of pH 8.0. Tests under different conditions (FIGS. 4–6) have indicated a marked correlation ($r^2$ of 0.963–0.994) between solution fluorescence and Fo values in the temperature range of 110°–138° C. Thus, by determining fluorescence of the solutions in the time-temperature indicator capsules placed inside food particulates, one obtains an accurate indication of the Fo values, and thereby determines whether the processed food has been rendered sterile from a microbial standpoint.

Figure 2:
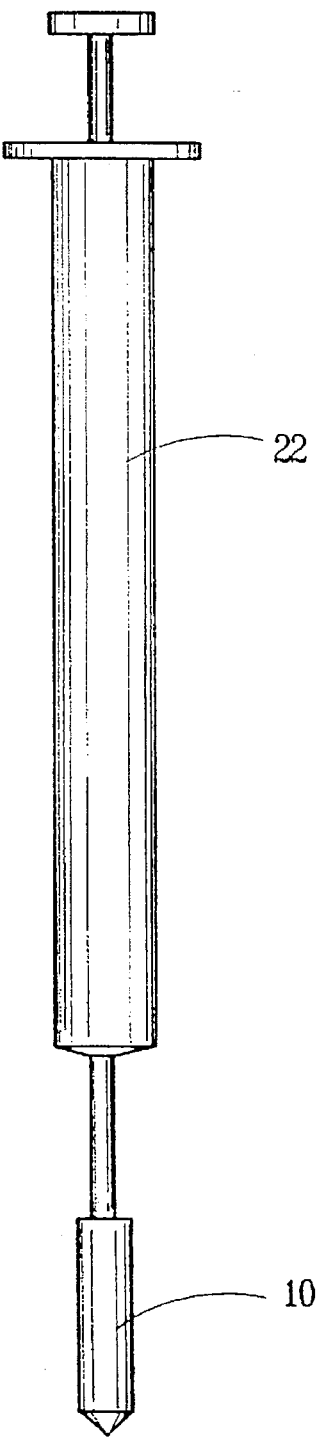
FIG. 2 is an elevational view of a known micro-pipetting device, shown in use with the capsule of FIG. 1.
Figure 3:
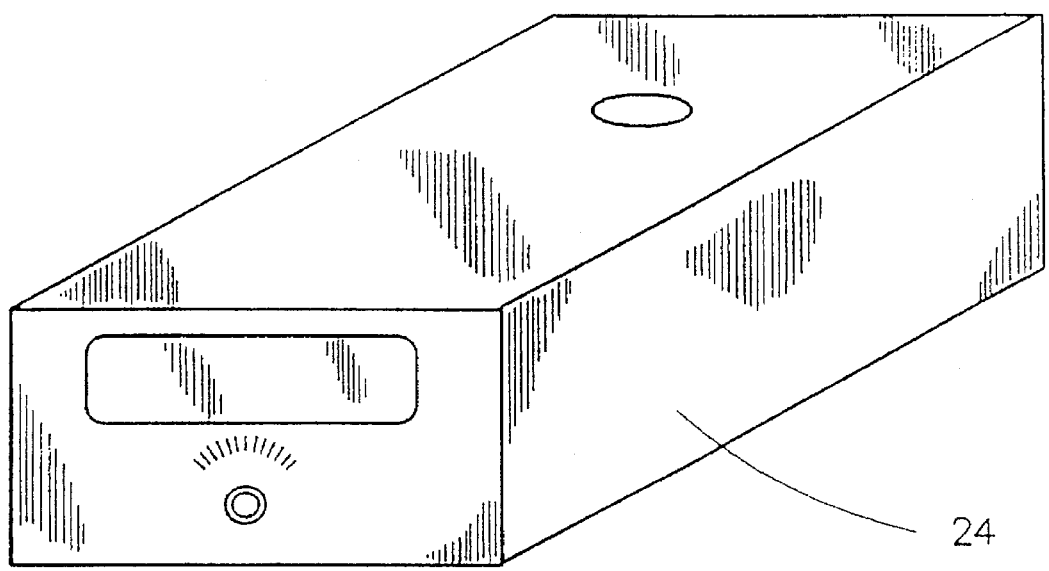
FIG. 3 is a diagrammatic representation of a known spectrofluorometer used in conjunction with the capsule and pipetting device of FIG. 2 to determine fluorescence of liquid contained in the capsule.

In food processing operation, the capsules may be placed inside particulates of, or proximate to, food prior to processing. At an approximate point in the processing line, such as at or near the end of the line, one or more capsules may be removed and opened. By a pipetting device, such as a known syringe 22 (FIG. 2), about 20 microliters of solution may be removed from a capsule and pipetted into 5–10 mL of deionized water, thoroughly mixed therewith, and read by a known spectrofluorometer 24 (FIG. 3).

Figure 4:
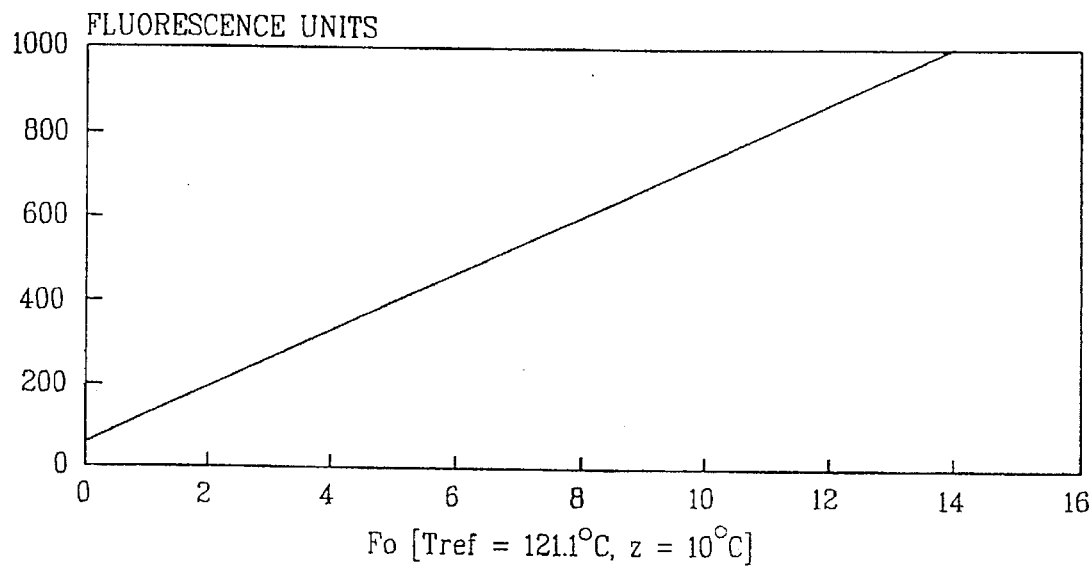
FIGS. 4–6 are graphs illustrating correlations between quinine sulfate standardized fluorescence units and Fo values at different temperatures from 121° C. to 138° C.
Figure 5:
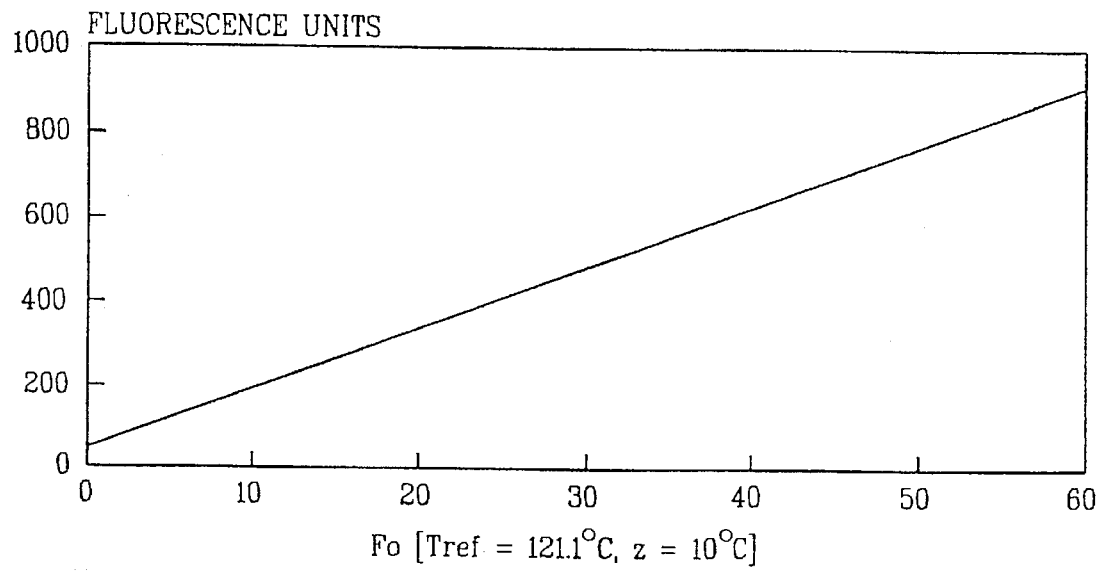
Figure 6:
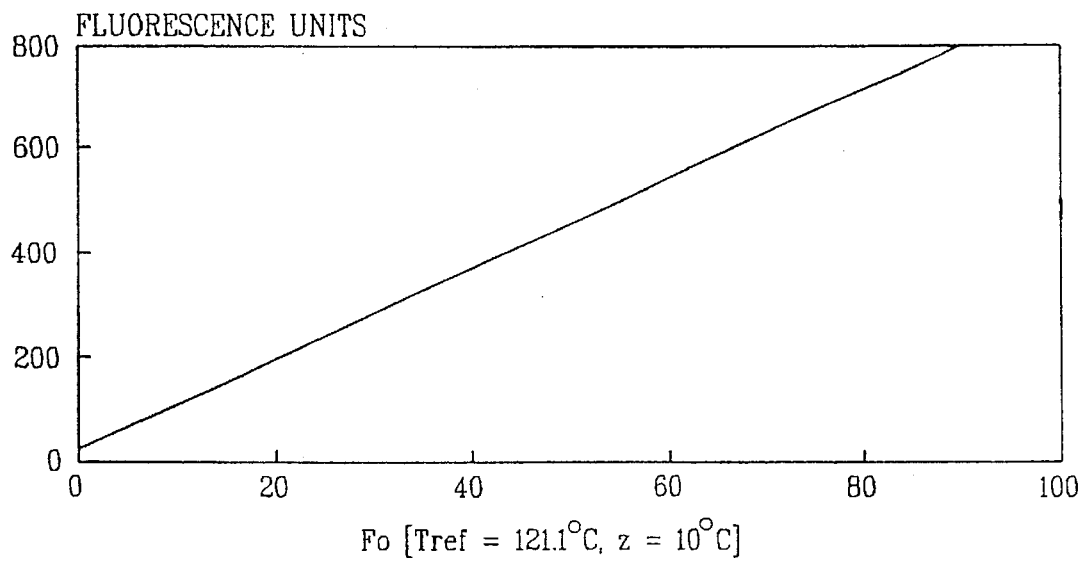
Figure 7:
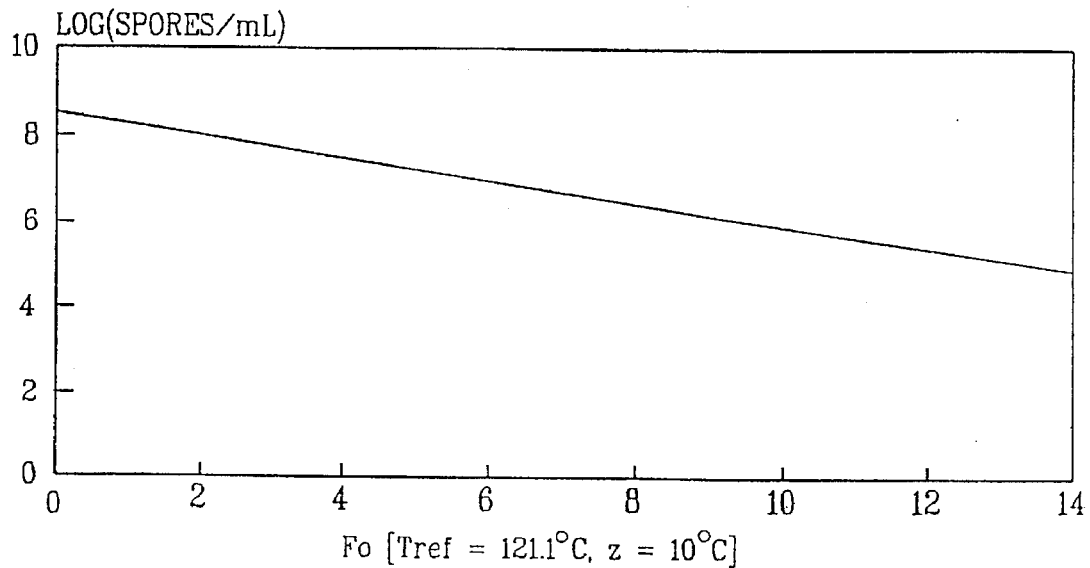
FIG. 7 is a graph illustrating correlations between the logarithm of the surviving spores and Fo values at 121° C.
Figure 8:
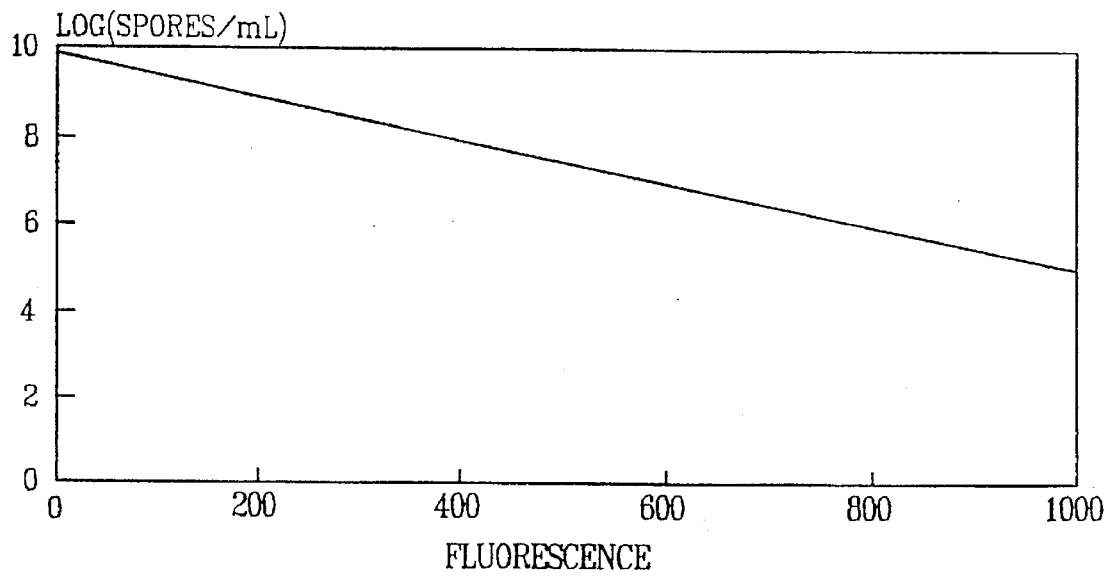
FIG. 8 is a graph illustrating correlations between the logarithm of the surviving spores and fluorescence values of lysine-glucose solutions heated concurrently at 121° C.

As is apparent from FIGS. 4–6, the fluorescence reading ($r^2$ of 0.963–0.994) provides a reliable and accurate indication of the aggregate thermal effect on the solution. It may be deduced from data, such as shown in FIGS. 7–8, that, when the capsules are inserted into food particulates, the fluorescence readings reflect the aggregate thermal effects on these particulates during heating or processing. Good correlation ($r^2=0.929$) between fluorescence and Fo values has been obtained with capsules containing lysine-glucose solution inserted into potato cylinders heated in water in jars in an autoclave at 121° C.

Experience has shown that the capsule 8 may be used hundreds of times, subject only to changing the nylon washer after 15–20 uses. Because of their small size, the capsules easily may be embedded in food particles. Because of the thin walls (about 1/64 inch) of the capsule and thickness of the capsule (radius of about 1/16 inch), transfer of heat to the solution 20 is rapid. While 20 microliters of solution are suggested for analysis by the spectrofluorometer, samples as small as 2 microliters have been found to provide reliable and accurate readings.

The capsule also provides a means of directly testing the lethality of a process and the sterility of a product through degradation of a solution of bacterial spores, such as 10^8/mL of *B. stearothermophilus*. The capsule is provided with a solution of bacterial spores, such as *B. stearothermophilus*, reactive to accumulated temperature and time exposure. The capsule is placed inside particulates of, or proximate to, food to be processed. The food is then subjected to temperatures in the range of 110° C. to 138° C. for a selected time period. After the selected time period, the capsule is removed from the food. A sample of the degraded solution is then pipetted from the capsule and plated onto an agar plate (not shown), well known in the art, having thereon an antibiotic assay medium supplement, which provides a count of the surviving spores, which count is indicative of the aggregate thermal effect on the solution. Tests conducted with TTICs containing these spore solutions and heated at temperatures of 121° C. and 133° C. have consistently shown a good correlation ($r^2$=0.894 to 0.962) between logarithm of surviving spores and Fo values. As illustrated in FIGS. 7 and 8, the lethality of heating operations may be readily estimated from the number of spores within the capsules that survive such treatment. The logarithm of the surviving spores are proportional to both Fo ($r^2$=0.941) and to fluorescence ($r^2$=0.902) of lysine-glucose solution heated concurrently in separate capsules under identical conditions in a convection oven or placed inside potato cylinders in water in an autoclave at 121° C. The sterility of cold spots within a number of fast moving large particulates can be individually confirmed by making use of these capsules containing appropriate spore solutions.

The TTICs may be numbered to facilitate easy identification, tracking and reconstruction of the chronological order of movement of food particulates in a continuous flow process system.

It is to be understood that the present invention is by no means limited to the particular construction and methods herein disclosed and/or shown in the drawings, but also comprises any modifications or equivalents within the scope of the claims. For example, the dimensions of the capsule may vary, according to need. An alternative size of capsule found to be useful is provided with a length of about ½ inch and a radius of about 1/32 inch, with a capacity of about 10 microliters.

What is claimed is:

1. Method for determining when pathogenic bacterial spores contained in food processed under high temperature conditions have been reduced to a level of microbial population rendering said food sterile, said method comprising the steps of:

providing at least one steel capsule of substantially cylindrical shape having a closed beveled end and an open end with a cap threadedly engageable to an inside surface of said open end said steel capsule being, no more than about 0.75 inch long, having an external radius of not more than about 0.0625 inch and wall thickness no less than about 0.015625 inch, capable of being embedded in food particulates, and having a single chamber therein with a capacity of not more than about 25 microliters;

providing in said chamber a solution reactive to accumulated temperature and time exposure to fluoresce proportionally to said accumulated temperature and time exposure, said fluorescence correlating to an $F_0$ value, and closing the chamber with the cap;

placing said capsule inside particulates of, or proximate to said food;

processing said food by subjecting said food to temperatures in the range of 110° C. to 138° C. for a time period;

removing said capsule from said processing after said time period;

pipetting a sample of said solution from said capsule;

diluting said pipetted solution with deionized water; and placing said diluted solution in a spectrofluorometer to obtain, by reading the fluorescence of said pipetted and diluted solution and directly correlating the fluorescence to an $F_0$ value by linear regression, the cumulative effects of the time and temperature to which said food was exposed.

2. The method in accordance with claim 1 wherein said solution sample comprises 2–25 microliters of said solution.

3. The method in accordance with claim 2 wherein said solution is comprised of lysine, glucose and a buffer.

4. The method in accordance with claim 3 wherein the concentration of lysine is about 0.05 molar, glucose is about 0.15 molar, and the pH of the buffer is about 8.0.

5. The method in accordance with claim 2 wherein the steel capsule has a length of between about 0.5 inch and about 0.75 inch, a radius of between about 0.03125 inch and about 0.0625 inch, and a wall thickness of about 0.015625 inch.

6. The method in accordance with claim 1 wherein said solution sample comprises about 20 microliters of said solution.

7. The method in accordance with claim 6 wherein said deionized water comprises 5–10 mL of said water.

8. The method in accordance with claim 7 wherein said solution is comprised of lysine, glucose and a buffer.

9. The method in accordance with claim 8 wherein the concentration of lysine is about 0.05 molar, glucose is about 0.15 molar, and the pH of the buffer is about 8.0.

10. The method in accordance with claim 6 wherein the steel capsule has length of between about 0.5 inch and about 0.75 inch, a radius of between about 0.03125 inch and about 0.0625 inch, and a wall thickness of about 0.015625 inch.

11. The method in accordance with claim 6 wherein said solution is comprised of lysine, glucose and a buffer.

12. The method in accordance with claim 11 wherein the concentration of lysine is about 0.05 molor, glucose is about 0.15 molar, and the pH of the buffer is about 8.0.

13. The method in accordance with claim 1 wherein said solution is comprised of lysine, glucose and a buffer.

14. The method in accordance with claim 13 wherein the concentration of lysine is about 0.05 molar, glucose is about 0.15 molar and the pH of the buffer is about 8.0.

15. The method in accordance with claim 1 wherein the steel capsule has a length of between about 0.5 inch and about 0.75 inch, a radius of between about 0.03125 inch and about 0.0625 inch, and a wall thickness of about 0.015625 inch.

* * * * *